United States Patent [19]

Mori

[11] Patent Number: 4,838,271

[45] Date of Patent: Jun. 13, 1989

[54] VISIBLE LIGHT RAY RADIATION DEVICE FOR USE IN MEDICAL TREATMENT

[76] Inventor: Kei Mori, 3-16-3-501, Kaminoge, Setagaya-ku, Tokyo, Japan

[21] Appl. No.: 126,387

[22] Filed: Nov. 30, 1987

[30] Foreign Application Priority Data

Dec. 10, 1986 [JP] Japan .................................. 61-293899

[51] Int. Cl.⁴ ............................................. A61N 33/00
[52] U.S. Cl. ...................................... 128/398; 362/32; 362/397
[58] Field of Search ........................ 128/24.1, 395–398; 351/223; 362/32, 397

[56] References Cited

U.S. PATENT DOCUMENTS 1,746,893  2/1930  Homan ................................. 128/395
3,903,870  9/1975  Berndt ................................. 351/223

FOREIGN PATENT DOCUMENTS 2740969  3/1979  Fed. Rep. of Germany ...... 128/398

Primary Examiner—Edward M. Coven
Assistant Examiner—M. Graham
Attorney, Agent, or Firm—Jordan and Hamburg

[57] ABSTRACT

A visible light ray radiation device for use in medical treatment comprises one large optical conductor cable having many smaller optical conductor cables within it, a hollow, transparent, resilient, skirted member, and an air-suction member. The large optical cable is unbound at the end side of it into many smaller optical conductor cables. The skirted member is attached to the end of each smaller optical conductor cable. An air-suction member is attached respectively to each transparent member in order to reduce the inner pressure of the transparent member when the transparent member is attached to the areas of the skin to be cured.

1 Claim, 3 Drawing Sheets

VISIBLE LIGHT RAY RADIATION DEVICE FOR USE IN MEDICAL TREATMENT

BACKGROUND OF THE INVENTION

The present invention relates to a visible light ray radiation device for use in medical treatment, and in particular, a visible light ray radiation device capable of radiating only the light ray components corresponding to the visible light rays contained in the sun's rays onto the respective portions (desired portions) of the human body simultaneously.

The present applicant has previously proposed various ways to focus solar rays or artificial light rays by the use of lenses or the like, to guide the same into an optical conductor cable, and thereby to transmit and emit the same onto an optional desired place. The solar rays or the artificial light rays transmitted and emitted in such a way are employed for illumination or other like purposes, as for example for cultivating plants, chlorella and the like. In the process of the above-mentioned light ray transmission, the visible light ray components of the sun's rays, containing therein neither ultraviolet nor infrared rays, promotes the health of a person by producing a living body reaction and the same prevents the skin of a human body from growing old. Furthermore, the visible light ray components create the noticeable effect of helping patients recover from arthritis, neuralgia, bedsores, rheumatism, injuries, bone fractures and alleviate pain from those diseases as well. Such beneficial effects have already been witnessed by the present applicant.

On the basis of the above-mentioned discovery, the present applicant has previously proposed in various ways a light ray radiation device for use in medical treatment capable of administering various medical treatments or beauty treatments and for promoting the health of a human body by radiating the light rays corresponding to the visible light ray components of the sun's rays, containing therein no harmful components such as ultraviolet rays, infrared rays and the like.

A light ray radiation device for use in medical treatment previously proposed by the present applicant comprises an optical conductor cable, a semi-transparent or transparent cylindrical member and a cover member. The solar rays or the artificial light rays are guided into the optical conductor cable at the end portion thereof, and the guided light rays are transmitted therethrough. The light rays corresponding to the visible light ray components of the sun's rays (while light rays) are transmitted into the optical conductor cable in the manner previously proposed by the present applicant. The semi-transparent or transparent cylindrical member is furnished at the light-emitting end portion of the afore-mentioned optical conductor cable and the cover member is provided for closing off one end of the cylindrical member. The light-emitting end portion of the optical conductor cable is attached to the cover member at the almost central portion thereof. The solar ray energy transmitted through the optical conductor cable is discharged into the cylindrical member. At the time of administering medical treatment, the other end of the cylindrical member is put on the part of the body to be cured, or the same is placed opposite to the part to be cured and at the desired interval therefrom. The light rays consisting of the visible light ray components transmitted through the optical conductor cable are radiated onto a diseased part of the body or desired portion to be cured. The light rays to be radiated onto the diseased part of a patient are the light rays corresponding to the visible light ray components of the sun's rays which contain therein neither ultraviolet nor infrared rays. Consequently, it is possible to administer medical treatment without endangering the health of a patient.

SUMMARY OF THE INVENTION

The primary object of the present invention is to further improve the light ray radiation device for use in medical treatment as mentioned above.

Another object of the present invention is to provide a visible light ray radiation device for use in medical treatment capable of radiating the light rays therefrom at the same time onto a large number of diseased parts of a human body.

Another object of the present invention to provide a visible light ray radiation device for use in medical treatment capable of radiating for a long time simultaneously and stably onto a large number of desired portions of the human body by using a simple and low-cost construction.

Another object of the present invention to provide a visible light ray radiation device for use in medical treatment capable of observing easily the condition of radiation at the respective light ray radiation spots through a transparent skirted member.

DESCRIPTION OF THE PREFERRED EMBODIMENTS

Figure 1:
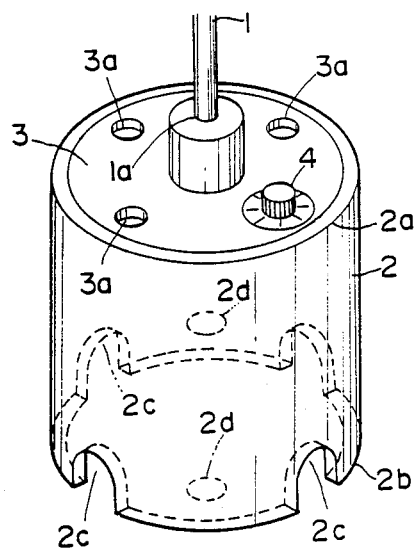
FIG. 1 is a construction view for explaining an embodiment of the conventional visible light ray radiation device for use in medical treatment.

FIG. 1 is a construction view for explaining an embodiment of the light ray radiation device for use in medical treatment previously proposed by the present applicant. In FIG. 1, 1 is an optical conductor cable. The solar rays or the artificial light rays are guided into the optical conductor cable 1 at the end portion thereof not shown in FIG. 1, and the guided light rays are transmitted therethrough. The light rays corresponding to the visible light ray components of the sun's rays (white light rays) are transmitted into the optical conductor cable 1 in the manner previously proposed by the present applicant. In FIG. 1, 2 is a semi-transparent or transparent cylindrical member furnished at the light-emitting end portion 1a of the afore-mentioned optical conductor cable 1, and 3 is a cover member for closing off one end 2a of the cylindrical member 2. The light-emitting end portion 1a of the optical conductor cable 1 is attached to the cover member 3 at the almost central portion thereof. The solar ray energy transmitted through the optical conductor cable 1 is discharged into the cylindrical member 2. At the time of administering medical treatment, the other end 2b of the cylindrical member is put on the part of the body to be cured, or the same is placed opposite to the part to be cured and at the desired interval therefrom. The light rays consisting of the visible light ray components transmitted through the optical conductor cable 1, in such a manner as mentioned before, are radiated onto a diseased part of the body or desired portion to be cured. The light rays to be radiated onto the diseased part of a patient are the light rays corresponding to the visible light ray components of the sun's rays which contain therein neither ultraviolet nor infrared rays. Consequently, it is possible to administer medical treatment without endangering the health of a patient.

Figure 2:
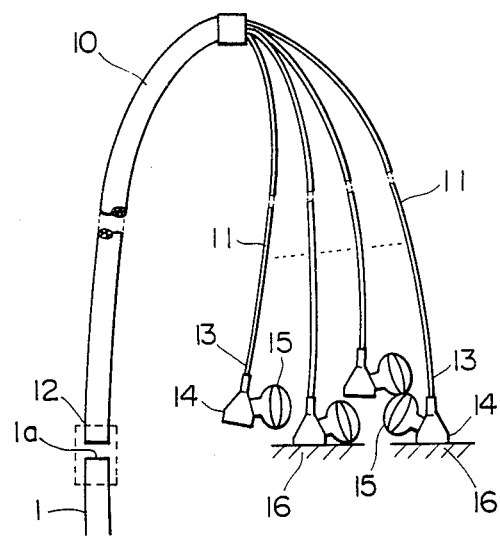
FIG. 2 is a construction view for explaining an embodiment of the visible light ray radiation device for use in medical treatment and according to the present invention.

FIG. 2 is a construction view for explaining an embodiment of the visible light ray radiation device for use in medical treatment according to the present invention. In FIG. 2, 1 is an optical conductor cable through which the light rays corresponding to the visible light ray components of the sun's rays are radiated. One end (not shown in FIG. 2) of the optical conductor cable 1 is placed at the focal position of the lens which focuses the sun's ray or the light rays emitted from the artificial light ray source and which generates visible light ray components only. The end (not shown in FIG. 2) of the optical conductor 1 is moved along the light axis of the lense in order to adjust the position of the end surface so as to better utilize the sun's rays, for instance, only the light rays corresponding to the visible light ray components of the sun's rays are guided into the optical conductor cable 1. Specifically, the light rays not containing therein ultraviolet or infrared rays are guided into the optical conductor cable 1 and transmitted therethrough.

In FIG. 2, 10 represents an optical conductor cable for transmitting the visible light ray for use in medical treatment according to the present invention. The visible light ray radiation device for use in medical treatment comprises one large optical conductor cable 10 having many smaller optical conductor cables 11 within it which are unbound at the middle of said large optical conductor cable as shown in FIG. 2. On end 12 of the optical conductor cable 10 is unitarily constructed at the light-receiving end and the other ends 13 are constructed independently (i.e. at the light-emitting end). At the time of employing the visible light ray radiation device for administering medical treatment, the light-receiving end 12 is connected with the light-emitting end 1a of the optical conductor cable 1. The light rays, consisting of visible light ray components, transmitted through the optical conductor cable 1, are distributed into each conductor cable 11 of the visible light ray radiation device for administering medical treatment (according to the present invention). Then they are passed from the light-receiving end 12 to the light-emitting ends 13 of the optical conductor cables 11 and then supplied to an optional desired places.

The light rays, consisting of visible light ray components, guided into each optical conductor cable 11, are respectively discharged from the light-emitting end 13 of the respective optical conductor cables 11 and radiated onto a diseased part or a desired portion of the human body. In particular, in the case of radiating the light rays onto a desired portion, the number of desired portions may be many and therefore, it is more effective to radiate the visible light rays at exactly the same time onto all those portions. For this reason, the present invention guides the light rays (containing visible light ray components only) into a large number of optical conductor cables 11 simultaneously.

Furthermore the present invention can easily radiate simultaneously and stably the visible light ray components transmitted through a large number of optical conductor cables 11, as mentioned above, onto the desired portions of a human body. In the case of the embodiment shown in FIG. 2, a hollow, transparent, resilient, skirted member 14 and an air-suction member 15, for creating low pressure on the inside of the skirted member are attached to the light-emitting end 13 of the respective optical conductor cables 11. At the time of employing the device, the skirted member 14, attached to the light-emitting end 13 of the respective optical conductor cables 11, are mounted in order on each desired portion of the human body 16.

The method of mounting the skirted member 14 on the human body is as follows. Before placing a skirted member directly onto the desired portion of the human body 16, the air-suction member 15 is pressed and air contained in the air-suction member 15 is removed and then the skirted member is placed onto the skin. After the skirted member is placed onto the skin, the air-suction member is released so that the air in the skirted member is removed to the air-suction member thereby creating a vacuum inside the skirted member and causing it to be attached to the portion of the body to be cured. The pressure of the air contained in the skirted member has thereby become lower than the atmospheric pressure making it possible to attach the skirted member securely to the desired portion of the body.

Subsequently, the light-emitting ends of the optical conductor cables are fixed to the desired portions of the body in the same way, and thereby the visible light ray components can be radiated simultaneously onto a large number of desired portions of the human body. Furthermore, according to the present invention, each skirted member 14 is constructed of a transparent body. Thereby, the condition of radiation at the respective light ray radiation spots can be easily observed.

As is apparent from the foregoing description, according to the present invention, visible light ray components can be radiated for a long time simultaneously and stably onto a large number of desired portions of the human body by using a simple and low-cost construction.

Figure 3:
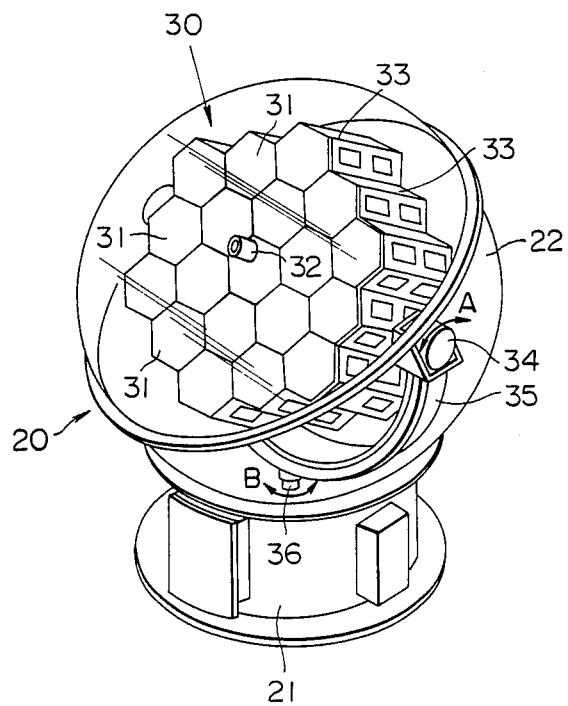
FIG. 3 is a perspective view showing the outline of the solar ray collecting device.

FIG. 3 is a perspective view for explaining the embodiment of a capsule employed with the solar ray collecting device which had been previously proposed by the present applicant. In FIG. 3, 20 is a capsule, 21 is a cylindrical base portion of the capsule, and 22 is a transparent dome-shaped head portion of the capsule. The capsule 20 employed with the solar ray collecting device 30 is constructed of base portion 21 and head portion 22. A solar ray collecting device 30 is accommodated in the capsule 20, as shown in FIG. 3, at the time of employing the device 30.

The solar ray collecting device 30 comprises a large number of lenses (for instance, nineteen lenses) 31 for focusing the sun's rays, a direction sensor 32 for sensing the direction of the sun, a supporting frame 33 for unitarily supporting those lenses 31 and the sensor 32, a first motor 34 for rotating those elements in the direction shown by arrow A, a holding arm 35 for holding the afore-mentioned lenses 31 onto the motor 34, a rotatable shaft 36, disposed so as to intersect perpendicularly to the rotatable shaft of the motor 34, and a second motor (not shown in FIG. 3) for rotating the rotatable shaft 36 in the direction shown by arrow B.

The direction of the sun is detected by the sensor 32, and its detection signal controls the afore-mentioned first and second motors so as to direct the lenses 31 toward the sun. The solar rays focused by the lenses 31 are guided into an optical conductor cable 1 in FIG. 2, the light-receiving end of which is disposed on the focal position of the lenses 31. The guided solar rays are transmitted through the optical conductor cable 1 to the optical desired place.

Figure 4:
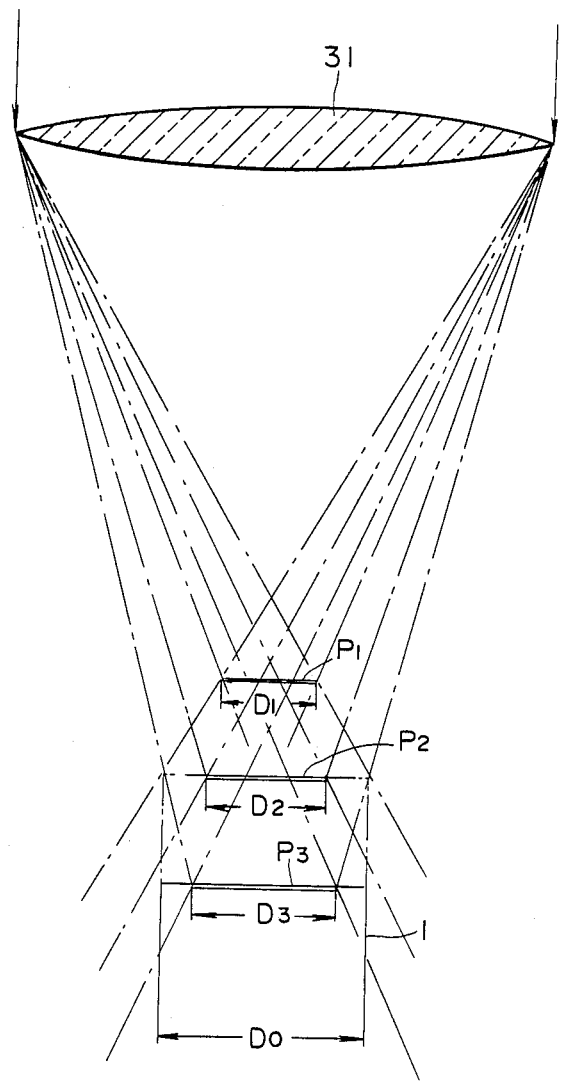
FIG. 4 is a visual explanatory view for explaining an embodiment of the visible light ray collecting method as applied to the present invention.

FIG. 4 is an explanatory view for explaining an embodiment of the device for guiding the afore-mentioned light rays, corresponding to the visible light ray components of solar rays, into the optical conductor cable 1. In FIG. 4, 31 is the same lens as that of the lens shown in FIG. 3 and the light rays focused by the lens 31 are guided into an optical conductor cable 1 for transmitting the solar rays therethrough. In the case of focusing the solar rays by use of a lens, the solar image has a central portion consisting of almost white-colored light rays and a circumferential portion containing therein a large amount of light ray components consisting of the needed wave lengths for focusing the lens system.

Namely, in the case of focusing the solar rays, its focal position and the size of the solar image will vary in accordance with the wave length of the light rays. For instance, the light rays of the color blue, having a short wave length, make a solar image of diameter $D_1$ at the position $P_1$. Furthermore, the light rasy of the color green make a solar image of diameter $D_2$ at position $P_2$ and the light rays of the color red make a solar image of diameter $D_3$.

Consequently, as shown in FIG. 4, when the light-receiving end-surface of the optical conductor cable 1 is put at position $P_1$, it is possible to collect solar rays containing plenty of light rays of the blue color component at the circumferential portion. When the same is put at position $P_2$, it is possible to collect solar rays containing plenty of light rays of the green color component at the circumferential portion. When the same is put at position $P_3$, it is possible to collect solar rays containing plenty of light rays of the red color component at the circumferential portion. In each case, the diameter of the optical conductor cable is determined by the light ray components to be collected. Therefore the diameter thereof is $D_1$, $D_2$ or $D_3$, depending on the color of the light ray stressed. In such a way, the use of the optical conductor cable can be reduced, and thereby solar rays containing plenty of light rays of the desired color can be collected most effectively. And further, as shown in FIG. 4, if the diameter of the light-receiving end-surface of the optical conductor cable is enlarged to $D_1$, it is possible to collect visible light rays containing all of the wave length components.

I claim:

1. A solar-ray energy radiation device for the application of the visible light rays component of solar rays to localized areas of a person's body, comprising a solar-ray collecting device for collecting the visible light rays component of solar rays from which ultraviolet rays and infrared rays have been excluded, optical conductor means receiving said visible light rays component, said optical conductor means having a light-emitting end portion, optical cable means comprising a bundled section and an unbundled section, said bundled section comprising a plurality of bundled cables, said bundled section having one end juxtaposed to said light-emitting end portion of said optical conductor means such that said visible light rays component is transmitted from said light-emitting end portion to said bundled section, said unbundled section comprising a plurality of separate and independent unbound optical cables each separately movable relative to one another, each of said unbound optical cables being a continuation of one of the plurality of optical cables which constitute said bundled section, each of said unbound optical cables having an end portion, a hollow skirted member made of a transparent resilient material attached to each of said end portions of each of said unbound optical cables, each of said end portions having a light-emitting end disposed within said hollow skirted member for emitting said visible light rays component within said hollw skirted member, and air suction member attached to each of said hollow skirted members for effecting a reduced pressure in the respective hollow skirted member, said skirted member being adapted to be placed on the skin of a person being treated, said reduced pressure and the resulting vacuum in said hollow skirted member holding said hollow skirted member to said person's skin, whereby each of said skirted members may be placed and held on different locations of said person's skin as each of said light-emitting ends of each of said unbound optical cables emit said visible light rays component onto localized areas of a person's skin encompassed within each hollow skirted members with the condition of the light emission at each of said localized areas being readily observable through said transparent skirted member.

* * * * *